United States Patent [19]

Duffett

[11] Patent Number: Plant 5,621

[45] Date of Patent: Dec. 31, 1985

[54] CHRYSANTHEMUM PLANT NAMED VIM

[75] Inventor: William E. Duffett, Salinas, Calif.

[73] Assignee: Yoder Brothers, Inc., Barberton, Ohio

[21] Appl. No.: 571,184

[22] Filed: Jan. 16, 1984

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Vim particularly characterized as to uniqueness by the combined characteristics of flat capitulum form; decorative capitulum type; deep yellow ray floret color; diameter across face of capitulum ranging from 5 to 7 cm. at maturity; uniform nine week photoperiodic flowering response to short days; medium plant height when grown single stem; 12 to 15 cm. peduncles on open, normally terminal sprays; and 13° C. minimum temperature tolerance for initiation and development of flowering buds.

3 Drawing Figures

The present invention comprises a new and distinct cultivar of *Chrysanthemum morifolium*, Ramat., named Vim.

Vim is a product of a planned sport induction program which had the objective of creating a new chrysanthemum cultivar that would have yellow color derived from a bronze seedling while retaining all other original traits.

Vim was discovered and selected by William E. Duffett in April, 1980 in a controlled environment in Salinas, Calif. as one flowering plant, a color mutation, within a flowering block established as rooted cuttings from stock plants which had been exposed as unrooted cuttings to an X-ray source of 900 rads. The irradiated seedling was an unnamed bronze decorative, identified as 78768001, originated by the present inventor.

The first act of asexual reproduction of Vim was accomplished when vegetative cuttings were taken from the initial selection in July, 1980 in a controlled environment in Salinas, Calif. by a technician working under formulations established and supervised by William E. Duffett.

Horticultural examination of selected units initiated October, 1980 has demonstrated that the combination of characteristics as herein disclosed for Vim are firmly fixed and are retained through successive generations of asexual reproduction.

Vim has not been observed under all possible environmental conditions. The phenotype may vary significantly with variations in environment such as temperature, light intensity, and day length. The following observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Vim which in combination distinguish this chrysanthemum as a new and distinct cultivar:

(1) Flat capitulum form.

(2) Decorative capitulum type.

(3) Deep yellow ray floret color.

(4) Diameter across face of capitulum ranging from 5 to 7 cm. at maturity.

(5) Uniform nine week photoperiodic flowering response to short days.

(6) Medium peduncle length, ranging from 12 to 15 cm.

(7) Medium plant height, requiring 2 to 3 long day weeks prior to short days to attain a flowered plant height of 85 to 90 cm. for April through November flowerings.

(8) Low temperature tolerance of 13° C. for bud initiation and flower development when grown in single stem cut spray programs with a continuous dark period of 13 hours.

The accompanying photograhic drawings show typical inflorescence and leaf characteristics of Vim, with the colors being as nearly true as possible with illustrations of this type. Sheet 1 is a color photograph of Vim grown as a single stem cut spray. Sheet 2 is a black and white photograph of three views of the inflorescence of Vim. Sheet 3 is a black and white photograph showing the leaves of Vim at three stages of development (mature, intermediate and immature).

Of the many commercial cultivars known to the present inventor, the most similar in comparison to Vim is Golden Polaris.

Reference is made to attached Chart A which compares certain characteristics of Vim to those same characteristics of Golden Polaris.

It will be noted that Vim has a deeper inflorescence color, smaller capitulum diameter, shorter peduncle length, shorter plant height and faster response to controlled short days. The capitulum form and type are similar.

In the following description, color references are made to The Royal Horticultural Society Colour Chart. The color values were determined between 3:00 and 3:30 P.M. on Oct. 28, 1983 under 150 foot-candle light intensity at Salinas, Calif.

Classification:

*Botanical.*—*Chrysanthemum morifolium*, Ramat. cv Vim.

*Commercial.*—Decorative spray cut mum.

I. Inflorescence

A. *Capitulum.*—Form: Flat. Type: Decorative. Diameter across face: 5 to 7 cm.

B. *Corolla of ray florets.*—Color (General tonality from distance of three meters): Deep yellow. Color (abaxial): 9A-B. Color (adaxial): 7B-C.

C. *Corolla of disc florets.*—Color (mature): 2A. Color (immature: 1A.

D. *Reproductive organs.*—Androecium: Present disc florets only; scant pollen. Gynoecium: Present both ray and disc florets.

II. Plant:

A. *General appearance.*—Height: Medium; 70 to 75 cm., as a flowering plant from a rooted cutting, with no long days for April through November flowerings and maintaining a minimum nightly 13 continuous dark period.

B. *Foliage.*—Color (abaxial): 147A. Color (adaxial): 147B. Shape: Deeply lobed and moderately serrated.

CHART A
COMPARISON OF VIM AND GOLDEN POLARIS

| CULTIVAR | RAY FLORET COLOR | CAPITULUM FORM AND TYPE | SPRAY FORMATION |
|---|---|---|---|
| VIM | DEEP YELLOW | FLAT DECO-RATIVE | TERMINAL 12 to 15 cm. PEDUNCLES |
| GOLDEN POLARIS | MEDIUM YELLOW | FLAT DECO- | TERMINAL 15 to 20 cm. |

-continued

CHART A
COMPARISON OF VIM AND GOLDEN POLARIS

| CULTIVAR | DIAMETER ACROSS FACE OF CAPITULUM | PLANT HEIGHT | FLOWERING RESPONSE PERIOD |
|---|---|---|---|
| VIM | 5 to 7 cm. | MEDIUM 70 to 75 cm. | 9 WEEKS |
| GOLDEN POLARIS | 6.5 to 7.5 cm. | TALL 80 to 85 cm. | 9 to 10 WEEKS |

COMPARISONS MADE OF PLANTS GROWN AS SINGLE STEM SPRAY CUT MUMS WITH NO LONG DAYS IN SALINAS, CALIFORNIA

I claim:

1. A new and distinct plant of *Chrysanthemum morifolium,* Ramat., named Vim, as described and illustrated, and particularly characterized as to uniqueness by the combined characteristics of flat capitulum form; decorative capitulum type; deep yellow ray floret color; diameter across face of capitulum ranging from 5 to 7 cm. at maturity; uniform nine week flowering response; medium plant height when grown single stem; 12 to 15 cm. peduncles on open, normally terminal sprays; and 13° C. minimum temperature tolerance for initiation and development of flowering buds.

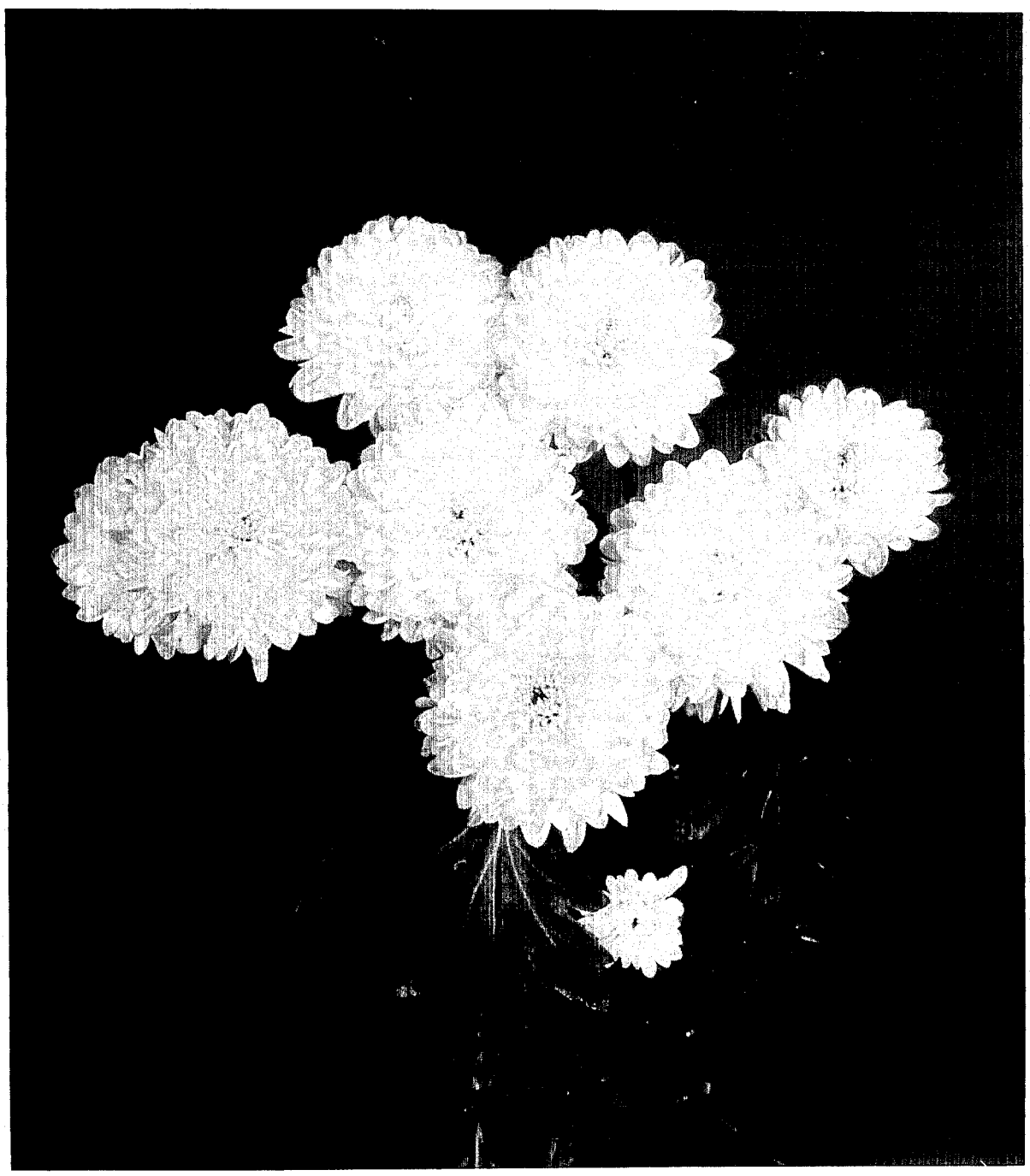

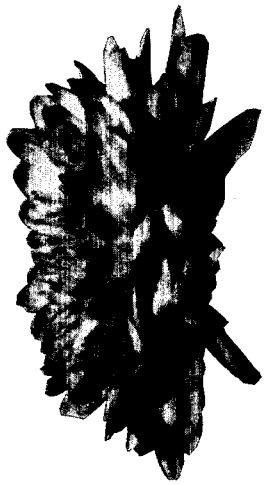
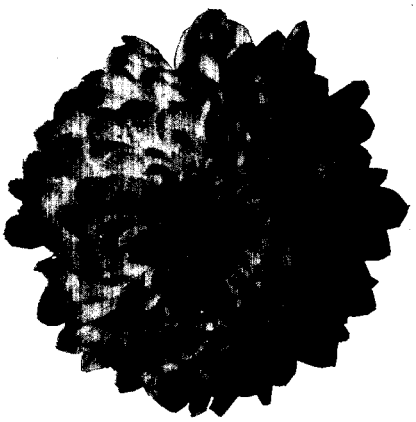
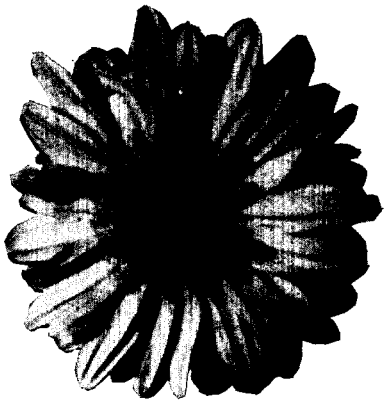

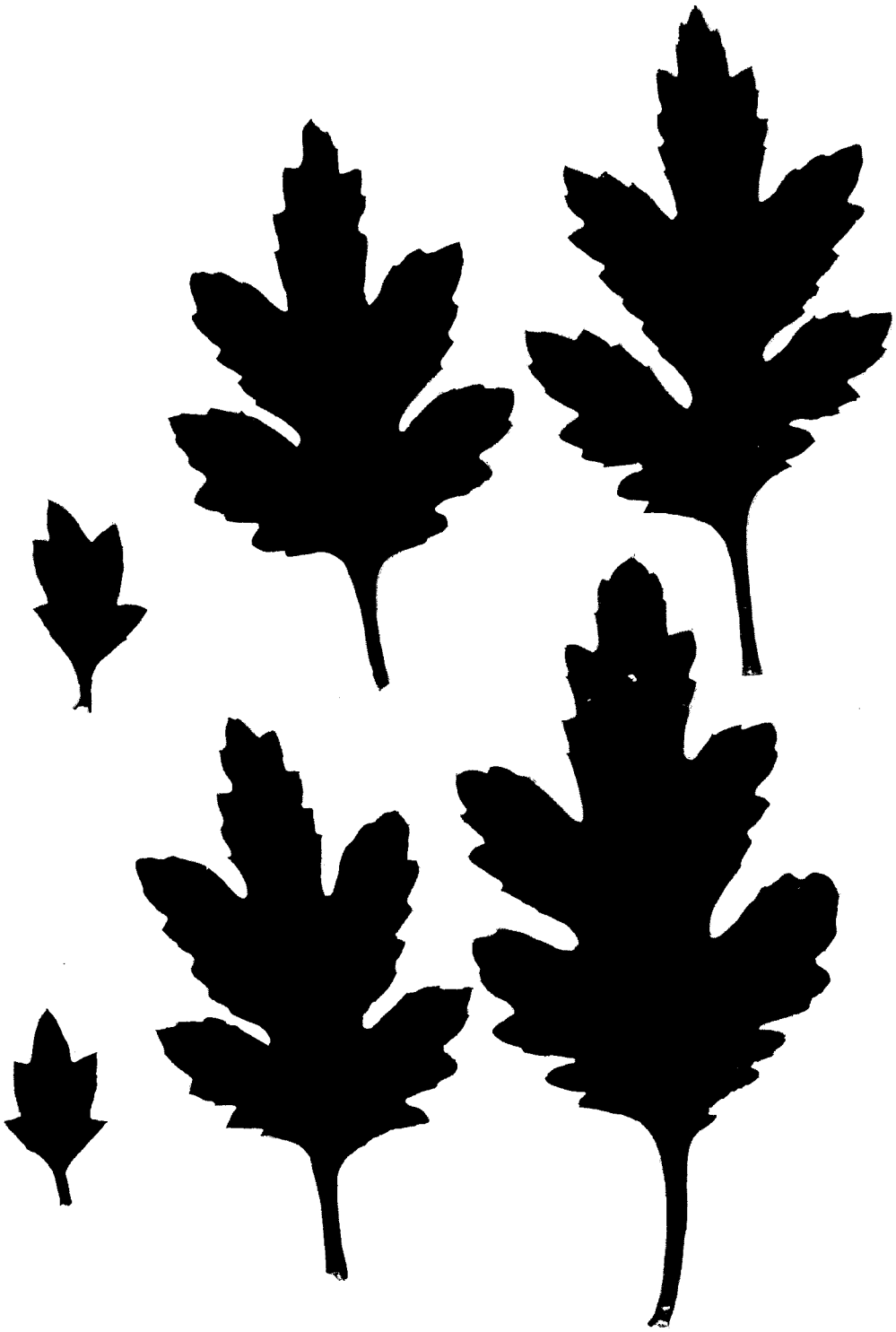

* * * * *